US00PP27133P2

(12) United States Plant Patent
Hendriksen

(10) Patent No.: US PP27,133 P2
(45) Date of Patent: Sep. 6, 2016

(54) ***ILEX* PLANT NAMED 'GDJ'**

(50) Latin Name: *Ilex aquifolium*
Varietal Denomination: GDJ

(71) Applicant: Simon Hendriksen, Hazerswoude (NL)

(72) Inventor: Simon Hendriksen, Hazerswoude (NL)

(73) Assignee: S. Hendriksen Beheer BV, Hazerswoude (NL)

( * ) Notice: Subject to any disclaimer, the term of this patent is extended or adjusted under 35 U.S.C. 154(b) by 0 days.

(21) Appl. No.: 14/544,597

(22) Filed: Jan. 26, 2015

(51) Int. Cl.
*A01H 5/00* (2006.01)

(52) U.S. Cl.
USPC ..... Plt./247

(58) Field of Classification Search
USPC ..... Plt./226, 247
See application file for complete search history.

(56) References Cited

PUBLICATIONS

PLUTO: Plant Variety Database, Feb. 9, 2016, citation for 'GDJ'. 1 page.*

* cited by examiner

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Ilex aquifolium*, 'GDJ', that is characterized by its well-branched, compact, and broadly upright plant habit, its variegated leaves that emerge with medium green centers with bright yellow-green margins and mature to dark green centers with yellow margins, and its leaves with a glossy surface.

2 Drawing Sheets

Botanical classification: *Ilex aquifolium.*
Cultivar designation: 'GDJ'.

BACKGROUND OF THE INVENTION

The present invention relates to a new and distinct cultivar of *Ilex* plant, botanically known as *Ilex aquifolium* 'GDJ' and will be referred to hereafter by its cultivar name, 'GDJ'. 'GDJ' represents a new herbaceous perennial grown for container and landscape use.

The Inventor discovered the new cultivar, 'GDJ', in 2011 as a naturally occurring branch mutation of the *Ilex aquifolium* cultivar 'Alaska' (not patented) in a container block at his nursery in Hazerswoude, The Netherlands.

Asexual reproduction of the new cultivar was first accomplished by stem cuttings by the Inventor in Hazerswoude, The Netherlands in 2011. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GDJ' as a new and distinct cultivar of *Ilex.*

1. 'GDJ' exhibits a well-branched, compact, broadly upright plant habit.
2. 'GDJ' exhibits variegated leaves that emerge with medium green centers with bright yellow-green margins and mature to dark green centers with yellow margins.
3. 'GDJ' exhibits leaves with a glossy surface.

The parent of 'GDJ', 'Alaska', differs from 'GDJ' in having leaves that are not variegated. 'GDJ' can most be most closely compared to the *Ilex aquifolium* cultivars 'Aureo Marginata' (not patented), 'Argentea Marginata' (not patented) and 'Northern Lights' (U.S. Plant Pat. No. 20,083). 'Aureo Marginata' differs from 'GDJ' in having a less compact and less branched plant habit and in having leaves that are larger in size with a less shiny surface. 'Argentea Marginata' differs from 'GDJ' in having larger leaves with margins that are white in color. 'Northern Lights' differs from 'GDJ' most significantly in having variegated foliage with yellow-green centers and dark green margins.

BRIEF DESCRIPTION OF THE DRAWINGS

The accompanying colored photographs illustrate the overall appearance and distinct characteristics of the new *Ilex*. The photographs were taken of a 1.5 year-old plant of 'GDJ' as grown in a field plot in, Hazerswoude, The Netherlands and placed in a container for the photographs.

The photograph in FIG. 1 provides a side-view of 'GDJ'.

Figure 1:
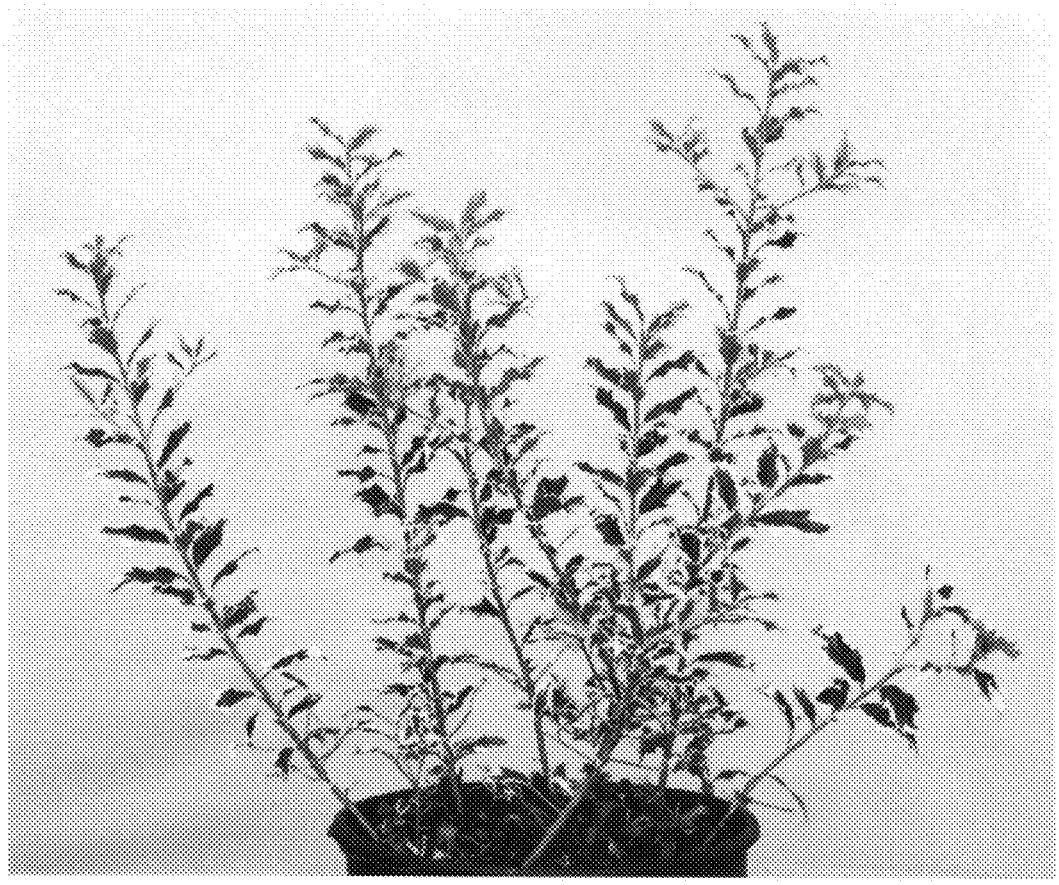
Figure 2:
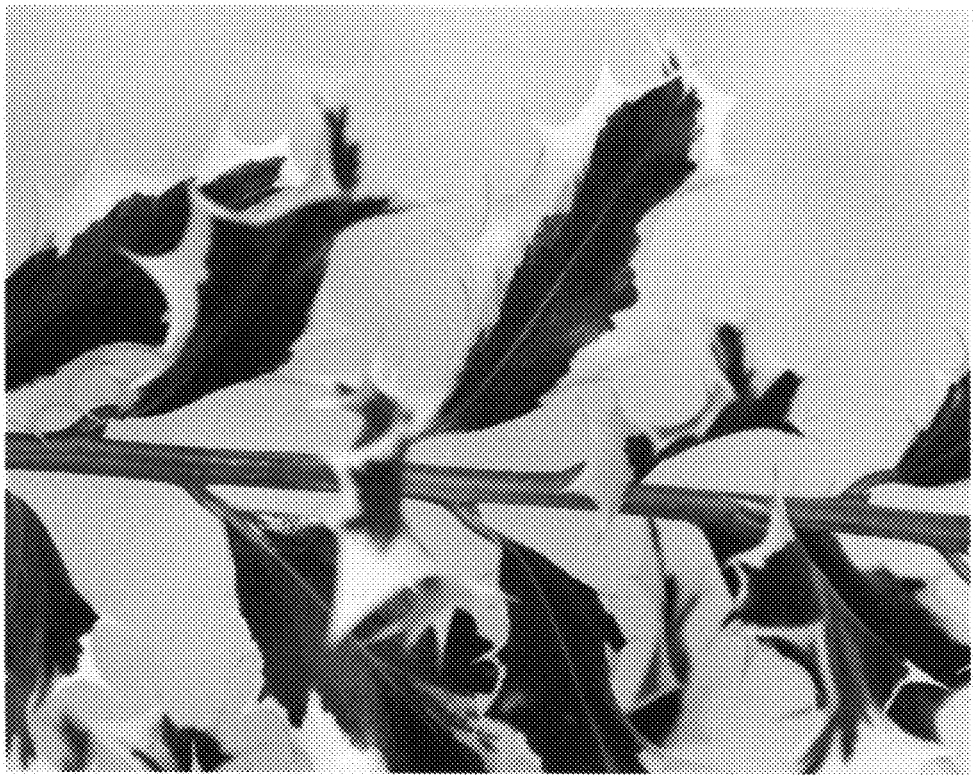

The photograph in FIG. 2 provides a close-up view of the mature leaves of 'GDJ'.

Figure 3:
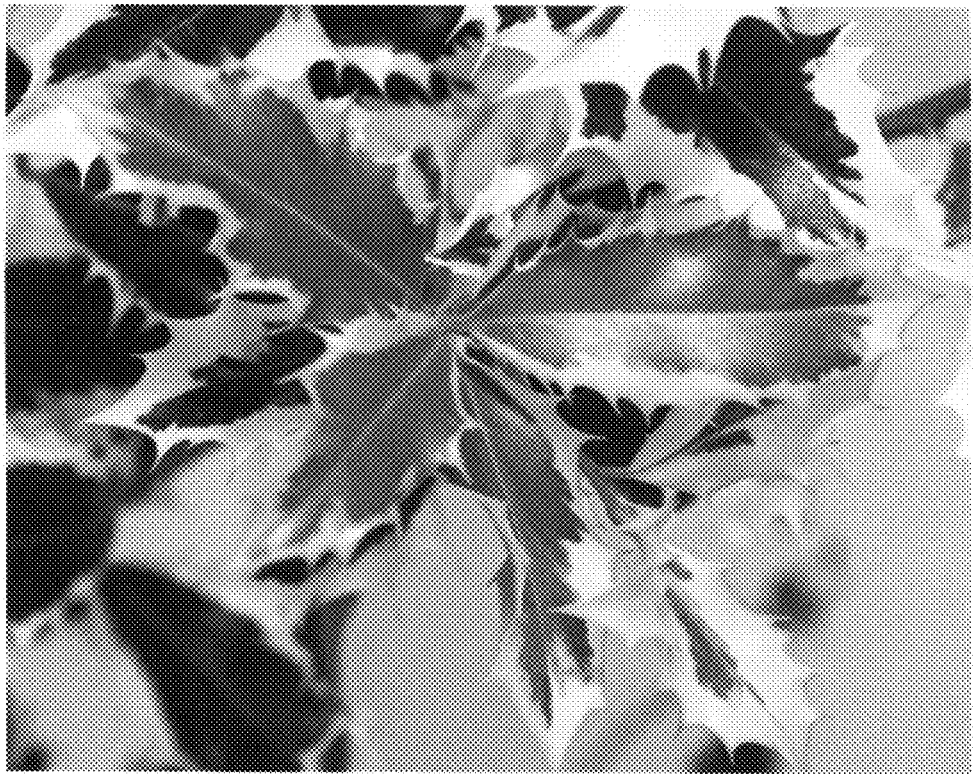

The photograph in FIG. 3 provides a close-up view of the young leaves of 'GDJ'.

The colors in the photographs are as close as possible with the digital photography techniques available, the color values cited in the detailed botanical description accurately describe the colors of the new *Ilex.*

DETAILED BOTANICAL DESCRIPTION OF THE PLANT

The following is a detailed description of 1.5 year-old plants of the new cultivar as grown outdoors in a field plot in Hazerswoude, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Plant type.*—Evergreen shrub.

*Plant habit.*—Compact, broadly upright.

*Height and spread.*—Reaches about 68.5 cm in height and 75.8 cm in spread.

*Cold hardiness.*—At least to U.S.D.A. Zone 5.

*Heat tolerance.*—At least tolerant to temperature up to 35° C.

*Diseases and pests.*—No particular resistance and susceptibility to pests and diseases has been observed.

*Root description.*—Slightly fibrous, not fleshy and fine, moderately dense and 161A in color.

*Root development.*—About 45 days to initiate roots at 25° C., young rooted plants are produced in 3 to 6 months.

*Growth rate.*—Moderate.

*Propagation.*—Stem cuttings.

Stem description:

*Shape.*—Round.

*Stem color.*—Young stem; N144D, axially striped 143A, mature stems, 138A, axially striped 145B.

*Stem size.*—An average of 25.6 cm in length and 4 mm in diameter.

*Stem surface.*—Smooth and very slightly glossy.

*Stem strength.*—Very strong.

*Internode length.*—An average of 1.2 cm.

*Branching habit.*—Freely branched, an average of 22 lateral branches.

Foliage description:

*Leaf shape.*—Ovate to elliptic.

*Leaf division.*—Simple.

*Leaf base.*—Cuneate.

*Leaf apex.*—Sharp acuminate and curved downward.

*Leaf venation.*—Pinnate, color on upper and lower surface 144A to 144B.

*Leaf margins.*—Undulate and sharply spinose, an average of 20 spines per leaf (10 on each side).

*Leaf attachment.*—Petiolate.

*Leaf arrangement.*—Alternate.

*Leaf aspect.*—Upright and outward, slightly recurved.

*Foliage fragrance.*—None.

*Leaf surface.*—Both surfaces glabrous thick and leathery.

*Leaf color.*—Young upper surface; a blend between 141A and 143A, margins and spines 151C, young lower surface; 146C to 146D, margins and spines 150C to 150D, mature upper surface; a blend between 147A and N189A, blotched with 147A, margins and spines 6D, mature lower surface; a blend between 138B and 191B to 191C, margins and spines 5D.

*Leaf size.*—An average of 7.3 cm in length and 3.8 cm in width.

*Leaf quantity.*—An average of 22 per lateral branch.

*Petioles.*—An average of 7 mm in length and 1.8 mm in width, color 144C, surface; smooth and slightly glossy.

Flower description: Flowers have not been observed to form on the new cultivar to date.

It is claimed:

1. A new and distinct cultivar of *Ilex* plant named 'GDJ' as herein illustrated and described.

* * * * *